United States Patent
You

(10) Patent No.: US 9,124,810 B2
(45) Date of Patent: Sep. 1, 2015

(54) METHOD OF CHECKING AN INSPECTION APPARATUS AND METHOD OF ESTABLISHING A MEASUREMENT VARIABLE OF THE INSPECTION APPARATUS

(75) Inventor: Hee-Wook You, Anyang-si (KR)

(73) Assignee: KOH YOUNG TECHNOLOGY INC., Seoul (KR)

(*) Notice: Subject to any disclaimer, the term of this patent is extended or adjusted under 35 U.S.C. 154(b) by 619 days.

(21) Appl. No.: 13/084,949

(22) Filed: Apr. 12, 2011

(65) Prior Publication Data
US 2011/0254949 A1   Oct. 20, 2011

(30) Foreign Application Priority Data

Apr. 14, 2010 (KR) .................. 10-2010-0034056
Mar. 16, 2011 (KR) .................. 10-2011-0023171
Apr. 8, 2011 (KR) .................. 10-2011-0032487

(51) Int. Cl.
| | |
|---|---|
| H04N 7/18 | (2006.01) |
| H04N 5/235 | (2006.01) |
| G01N 21/88 | (2006.01) |
| G01N 21/956 | (2006.01) |
| H04N 13/02 | (2006.01) |

(52) U.S. Cl.
CPC ......... *H04N 5/2354* (2013.01); *G01N 21/8806* (2013.01); *G01N 21/95684* (2013.01); *H04N 5/2351* (2013.01); *H04N 13/0253* (2013.01)

(58) Field of Classification Search
CPC .............. G01N 21/88; G01N 21/8806; G01N 21/95684; G06T 7/0004; H04N 13/0253; H04N 5/2351; H04N 5/2354

USPC .......... 348/E7.085, 135, 655, E5.074, 223.1, 348/370

See application file for complete search history.

(56) References Cited

U.S. PATENT DOCUMENTS

| | | | |
|---|---|---|---|
| 4,737,920 A | 4/1988 | Ozawa | |
| 6,542,248 B1 * | 4/2003 | Schwarz | 356/600 |
| 6,895,109 B1 * | 5/2005 | Schemmel et al. | 382/149 |
| 2002/0081025 A1 * | 6/2002 | Wagman | 382/170 |
| 2002/0105581 A1 * | 8/2002 | Masaki et al. | 348/229.1 |
| 2007/0009253 A1 * | 1/2007 | Nikkanen et al. | 396/234 |
| 2007/0291152 A1 * | 12/2007 | Suekane et al. | 348/333.02 |
| 2008/0278729 A1 * | 11/2008 | Kim | 356/450 |
| 2011/0054317 A1 * | 3/2011 | Lin et al. | 600/443 |

FOREIGN PATENT DOCUMENTS

| | | | | |
|---|---|---|---|---|
| EP | 1 081 742 | | 3/2001 | |
| JP | 02-145904 | * | 5/1990 | ............ G01B 11/24 |
| JP | 02-145904 | | 6/1990 | |

(Continued)

*Primary Examiner* — Mohammed Rahaman
(74) *Attorney, Agent, or Firm* — Kile Park Reed & Houtteman PLLC

(57) ABSTRACT

In order to establish a lighting intensity of an inspection apparatus, an inspection board is installed in an inspection apparatus. Then, a width of a histogram of a captured image acquired through a camera of the inspection apparatus is adjusted to avoid from a dark region and a bright region. Thereafter, a lighting intensity of the inspection apparatus is adjusted by adjusting the histogram to be near a middle of a graph. Thus, a setting time of an inspection condition stored in a job file may be reduced to increase the user's convenience, and measurement error due to mis-establishment may be reduced to enhance inspection precision.

8 Claims, 8 Drawing Sheets

(56) References Cited

FOREIGN PATENT DOCUMENTS

| | | |
|---|---|---|
| JP | 7-19825 | 1/1995 |
| JP | 10-148620 | 6/1998 |
| JP | 10-300686 | 11/1998 |
| JP | 11-072444 | 3/1999 |
| JP | 2001-202911 | 7/2001 |
| JP | 2003-139718 | 5/2003 |
| JP | 2007-333732 | 12/2007 |
| KR | 10-2009-0122266 | 11/2009 |
| TW | I319167 | 1/2010 |

* cited by examiner (a)

(b)

METHOD OF CHECKING AN INSPECTION APPARATUS AND METHOD OF ESTABLISHING A MEASUREMENT VARIABLE OF THE INSPECTION APPARATUS

CROSS REFERENCE TO RELATED APPLICATION

This application claims priority from and the benefit of Korean Patent Applications No. 2010-0034056 filed on Apr. 14, 2010, No. 2011-0023171 filed on Mar. 16, 2011 and No. 2011-0032487 filed on Apr. 8, 2011, which are hereby incorporated by reference for all purposes as if fully set forth herein.

BACKGROUND OF THE INVENTION

1. Field of the Invention

Exemplary embodiments of the present invention relate to a method of checking an inspection apparatus and a method of establishing a measurement variable of the inspection apparatus. More particularly, exemplary embodiments of the present invention relate to a method of checking a current condition of an inspection apparatus having a non-contact type using a light source and a camera, and establishing an optimized measurement condition corresponding to a characteristic of an inspection board.

2. Discussion of the Background

A mounting board, in which electronic parts are mounted on a printed circuit board (PCB), is used in various electronic devices. The mounting board is manufactured by a method of coating solder in a pad region of a bare board and then coupling terminals of electronic parts to a solder coating region.

Generally, in order to verify reliability of a PCB on which electronic parts are mounted, it is necessary whether the PCB is manufactured good or not before or after the electronic parts are mounted. For example, it is necessary to inspect whether solder is coated on the pad region of the PCB good or not before the electronic parts are mounted on the PCB, or whether the electronic parts are mounted good or not after the electronic parts are mounted on the PCB.

The inspection processes are performed by an inspection apparatus including an inspection probe having a light source providing light for inspection, a camera capturing an image, etc.

However, it may be incurred that a hardware condition of the inspection probe is changed by using the inspection apparatus for a long time, and inspection reliability is reduced. In addition, since PCBs have various colors and reflectances according to makers, it may be incurred that inspection reliability is reduced when inspecting PCBs of various characteristics by using the same inspection condition.

SUMMARY OF THE INVENTION

Exemplary embodiments of the present invention provide a method of checking an inspection apparatus, which checks a hardware condition of an inspection probe by using an automated test program and judges the current working condition of the inspection apparatus is proper or not in comparison with the time when the inspection apparatus is produced.

Exemplary embodiments of the present invention also provide a method of setting up a measurement variable of an inspection apparatus, which is capable of automatically re-establishing a measurement variable corresponding to a characteristic of an inspection board to reduce a time of setting up a job file, and enhancing inspection precision.

Additional features of the invention will be set forth in the description which follows, and in part will be apparent from the description, or may be learned by practice of the invention.

An exemplary embodiment of the present invention discloses a method of establishing a lighting intensity of an inspection apparatus. The method includes installing an inspection board in an inspection apparatus, adjusting a width of a histogram of a captured image acquired through a camera of the inspection apparatus to avoid from a dark region and a bright region, and adjusting a lighting intensity of the inspection apparatus by adjusting the histogram to be near a middle of a graph.

The method may further include adjusting the width of the histogram to be narrow.

The method may further include adjusting the lighting intensity of the inspection apparatus by using an effective index information having a parameter corresponding to an average of the lighting intensity. The effective index information may include visibility information. Adjusting the lighting intensity of the inspection apparatus by using the effective index information having the parameter corresponding to the average of the lighting intensity may include measuring visibility information while changing the lighting intensity of the inspection apparatus, and establishing the lighting intensity of the inspection apparatus with an intensity of lighting allowing a ratio of an effective pixel area to an area of an inspection region to exceed a pre-established effective value in the measured visibility information. After measuring the visibility information while changing the lighting intensity of the inspection apparatus, the method may further include visually indicating at least one of a region corresponding to effective pixels and a region not corresponding to the effective pixels in advance through the camera of the inspection apparatus by using the measured visibility information.

The lighting of the inspection apparatus may correspond to grating pattern lighting.

Before adjusting the width of the histogram of the captured image acquired through the camera of the inspection apparatus to avoid from the dark region and the bright region, the method may further include marking a first color at the dark region having a value smaller than or equal to a selected dark value, and a second color is marked at the bright region having a value greater than or equal to a selected bright value.

Another exemplary embodiment of the present invention discloses a method of establishing a lighting intensity of an inspection apparatus. The method includes installing an inspection board in an inspection apparatus, providing light to the inspection board while changing a lighting intensity of the inspection apparatus, acquiring the light reflected by the inspection board through a camera of the inspection apparatus and acquiring image data of the inspection board, acquiring measurement data for establishing the lighting intensity from the acquired image data of the inspection board, and establishing the lighting intensity of the inspection apparatus based on the measurement data.

The measurement data for establishing the lighting intensity may include at least one of a visibility and a gray scale.

In establishing the lighting intensity of the inspection apparatus based on the measurement data, the lighting intensity of the inspection apparatus may be established based on a visibility and a gray scale.

In establishing the lighting intensity of the inspection apparatus based on the measurement data, the lighting intensity of the inspection apparatus may be established with an intensity of lighting allowing the number of effective pixels, at which the measurement data are within a predetermined range, to be greater than or equal to a threshold in the image data of the inspection board.

In establishing the lighting intensity of the inspection apparatus based on the measurement data, the lighting intensity of the inspection apparatus may be established with an intensity of lighting allowing the number of effective pixels, at which the visibility and the gray scale are within a predetermined range, to be greater than or equal to a threshold in the image data of the inspection board.

Still another exemplary embodiment of the present invention discloses a method of checking an inspection apparatus. The method includes installing a setting target in an inspection apparatus, checking a hardware condition of the inspection apparatus, which includes at least one of a focus condition of a lighting, a moving condition of a grating-moving instrument, a uniformity condition of the lighting and an illumination intensity condition of the lighting by using a test program with respect to the setting target, and indicating the checked hardware condition of the inspection apparatus to a user.

The setting target may have at least one of a first region for checking the focus condition of the lighting, a second region for checking the moving condition of the grating-moving instrument, a third region for checking the uniformity condition of the lighting, and a fourth region for checking the illumination intensity condition of the lighting.

In indicating the checked hardware condition of the inspection apparatus, at least one of numericalized information of the checked hardware condition and grade information obtained by comparing the checked hardware condition with an initial hardware condition when the inspection apparatus is produced may be indicated.

According to the present invention, the current hardware condition of the inspection apparatus 100 is checked by using the automated test program, and thus it may be judged whether the current working condition is proper or not in comparison with the initial hardware condition when the inspection apparatus is produced. In addition, measurement variables such as lighting intensity, reference visibility, etc. corresponding to the inspection boards 150 having various characteristics are automatically re-established, thereby reducing a setting time of an inspection condition stored in a job file to increase the user's convenience and reducing measurement error due to mis-establishment to enhance inspection precision.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
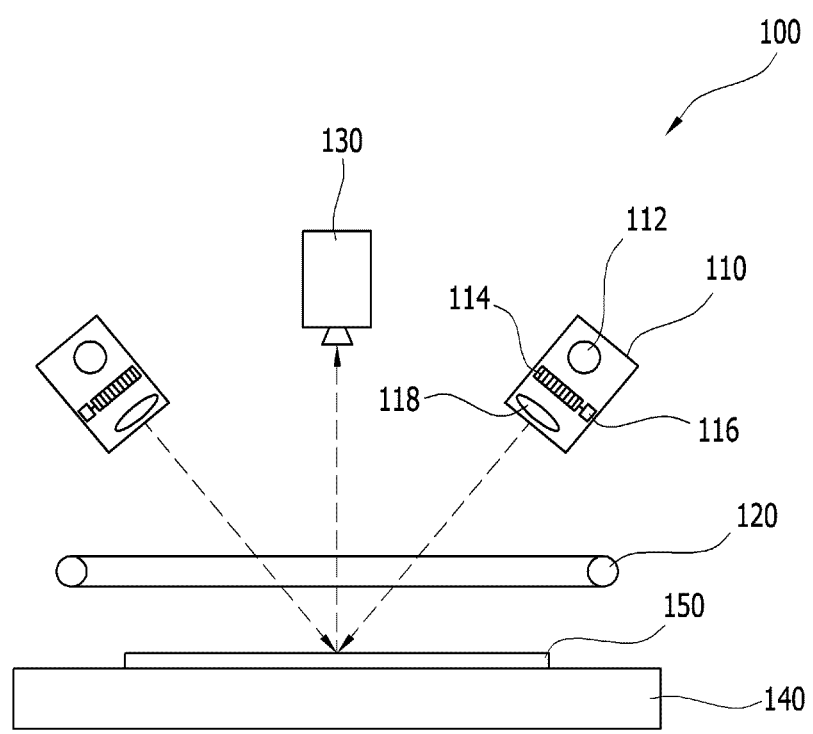
FIG. 1 is a schematic view illustrating an inspection apparatus according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

FIG. 1 is a schematic view illustrating an inspection apparatus according to an exemplary embodiment of the present invention. In FIG. 1, reference numeral 150 may be named for an inspection target, a setting target or an inspection board.

Referring to FIG. 1, an inspection apparatus 100 according to an exemplary embodiment of the present invention includes a stage 140 for supporting and moving an inspection target 150, at least one first lighting section 110 providing pattern light to the inspection target 150, a second lighting section 120 providing light for acquiring two-dimensional (2D) information to the inspection target 150 and at least one camera 130 receiving the light reflected from the light inspection target 150 and forming a pattern image and a plane image.

The first lighting section 110 provides the pattern light to the inspection target 150, to acquire three-dimensional (3D) information such as height information, visibility information, etc. of the inspection target 150. For example, the first lighting section 110 may include a light source 112 generating light, a grating element 114 converting the light from the light source 112 into pattern light, a grating-moving instrument 116 pitch-moving the grating element 114 and a projecting lens 118 for projecting the pattern light converted by the grating element 114 onto the inspection target 150. The grating element 114 may be moved using a grating-moving instrument 116 such as a piezoelectric (PZT) actuator by $2\pi/n$ per one time and n−1 times in total, for generating phase transition of the pattern light. The 'n' is a natural number greater than or equal to 2. A plurality of first lighting section 110 having the above-described structure may be disposed apart from each other by a substantially constant angle along a circumferential direction with respect to the center of the camera 130 so as to increase inspection accuracy.

The second lighting section 120 may have a circular ring shape, and installed adjacent to the stage 140. The second lighting section 120 provides light for acquiring 2D information to the inspection target 150, to set up an initial alignment, an inspection region, etc. of the inspection target 150. For example, the second lighting section 120 may include a fluorescent lamp generating white light or a light emitting diode (LED) including at least one of a red LED, a green LED and a blue LED generating red light, green light and blue light, respectively.

The camera 130 captures a pattern image of the inspection target 150 by the pattern light from the first lighting section 110, and captures a plane image of the inspection target 150 by the light for acquiring 2D information from the second lighting section 120. For example, the camera 130 is installed over the inspection target 150.

The inspection apparatus 100 having the above-described structure provides light to the inspection target 150 by using the first lighting section 110 and the second lighting section 120, and captures a reflection image of the inspection target 150 by the light by using the camera 130, to thereby acquire a 3D image and a 2D image of the inspection target 150. The inspection apparatus 100 illustrated in FIG. 1 is just an example, and may be modified having various structures, each of which includes at least one lighting section and a camera.

Hereinafter, a method of checking the inspection apparatus 100 having the above structure and a method of establishing a measurement variable of the inspection apparatus 100 will be described in detail.

Figure 2:
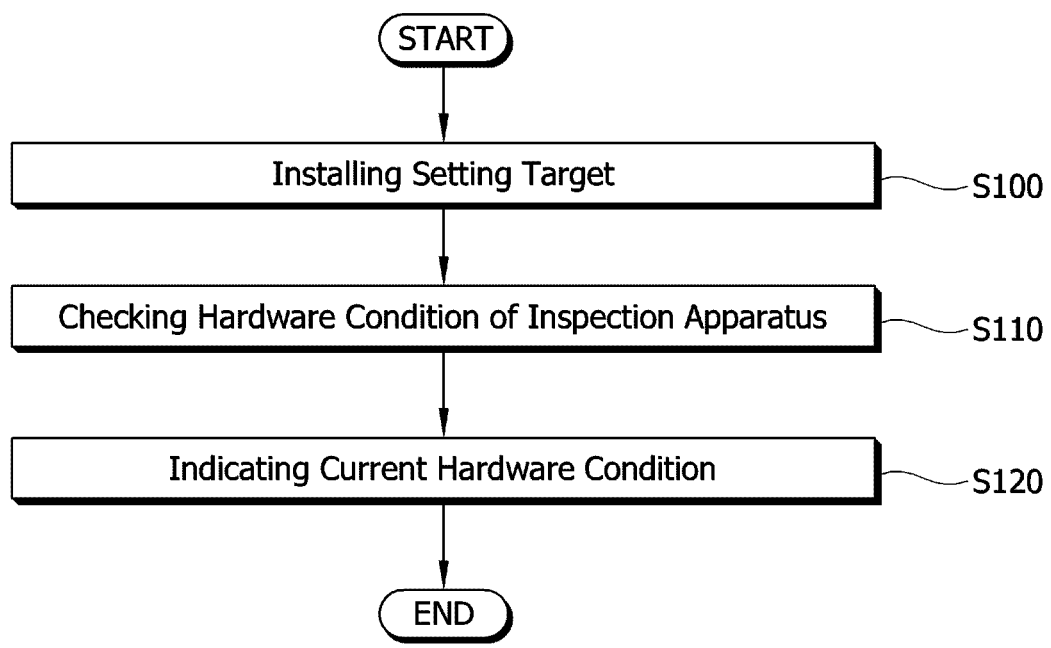
FIG. 2 is a flow chart showing a method of checking an inspection apparatus according to an exemplary embodiment of the present invention.

FIG. 2 is a flow chart showing a method of checking an inspection apparatus according to an exemplary embodiment of the present invention.

Referring to FIGS. 1 and 2, in order to check a current condition of the inspection apparatus 100, a setting target 150, which is independently manufactured for checking the inspection apparatus 100, is installed on the stage 140 in the inspection apparatus 100 in step S100.

Then, a hardware condition of the inspection apparatus 100 is checked by using an automated test program with respect to the setting target 150 in step S110. Particularly, the inspection apparatus 100 provides light to the setting target 150 installed on the stage 140 through the first lighting section 110 or the second lighting section 120. Thereafter, the inspection apparatus 100 captures an image through the camera 130, and analyzes the captured image, to check a hardware condition of an inspection probe in the inspection apparatus 100. For example, the inspection apparatus 100 automatically checks a current hardware condition such as a focus condition of the lighting including the first lighting section 110 or the second lighting section 120, a moving condition of the grating-moving instrument 116, a uniformity condition of the lighting and an illumination intensity condition of the lighting, etc. The focus condition of the lighting corresponds to a value calculated from a modulation transfer function (MTF) of a pattern projected onto the setting target 150 through the first lighting section 110 or the second lighting section 120. The moving condition of the grating-moving instrument 116 corresponds to a value obtained by numericalizing whether the moving of the PZT actuator has an equal interval or not when viewed at the camera 130. The uniformity condition of the lighting corresponds to a value obtained by numericalizing difference between the maximum value and the minimum value of the lighting in a field of view (FOV) of the camera 130. The illumination intensity condition of the lighting corresponds to a measurement variable for checking how the brightest illumination intensity at the current time is in comparison with predetermined minimum illumination intensity for satisfying measurement.

The setting target 150 may be divided into various regions to check various sorts of hardware conditions. For example, the setting target 150 may have a first region for checking the focus condition of the lighting, a second region for checking the moving condition of the grating-moving instrument 116, a third region for checking the uniformity condition of the lighting, and a fourth region for checking the illumination intensity condition of the lighting. A proper pattern may be formed in each region to check the associated hardware. In addition, at least two hardware conditions may be checked in one region.

After checking the hardware condition of the inspection apparatus 100, the current hardware condition is indicated to a user in step S120. For example, after checking the hardware condition of the inspection apparatus 100, at least one of numericalized information of the checked current hardware condition such as the focus condition of the lighting, the moving condition of the grating-moving instrument 116, the uniformity condition of the lighting and the illumination intensity condition of the lighting, etc., and grade information of the current hardware condition, which is obtained by comparing the checked current hardware condition with an initial hardware condition when the inspection apparatus is produced is indicated. The user may check a grade of the indicated hardware condition and judge whether maintenance of the associated hardware is required or not.

As described above, the current hardware condition of the inspection apparatus 100 is compared with the initial hardware condition when the inspection apparatus is produced and indicated to the user, by using the automated test program, and thus it may be judged whether the current working condition is proper or not.

In checking the inspection board 150 by using the inspection apparatus 100, measurement variables may be optimized corresponding to characteristics of the inspection board 150, since the characteristics such as color, reflectance, etc. are different according to the maker of the inspection board 150. The measurement variables may include, for example, a lighting intensity, a visibility, etc.

Figure 3:
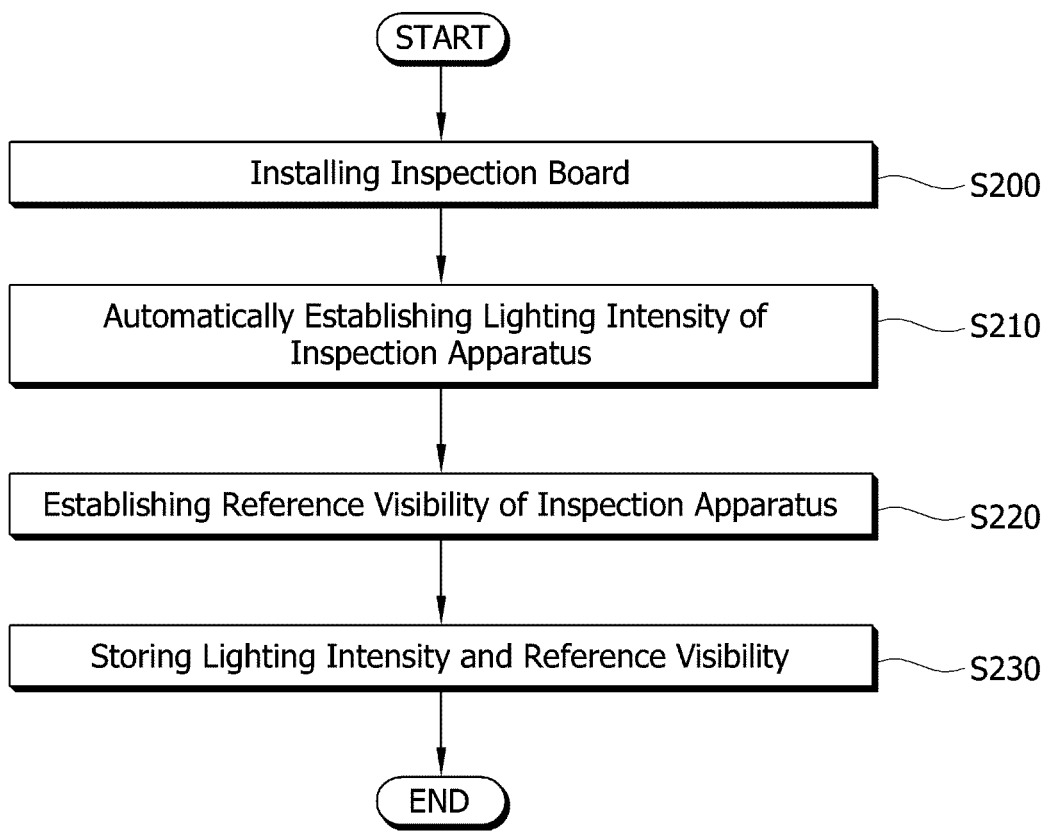
FIG. 3 is a flow chart showing a method of establishing a measurement variable of an inspection apparatus according to an exemplary embodiment of the present invention.

FIG. 3 is a flow chart showing a method of establishing a measurement variable of an inspection apparatus according to an exemplary embodiment of the present invention.

Referring to FIGS. 1 and 3, in order to establish a measurement variable of the inspection apparatus 100 corresponding to a characteristic of the inspection board 150, the inspection board 150 is installed on the stage 140 in the inspection apparatus 100 in step S200.

Then, a lighting intensity of the inspection apparatus 100 is automatically established corresponding to the characteristic of the inspection board 150 in step S210. Particularly, the inspection apparatus 100 provides light to the inspection board 150 installed on the stage 140 through the first lighting section 110 or the second lighting section 120, and acquires a captured image through the camera 130. In acquiring the captured image, after an inspection probe, including the first and second lighting sections 110 and 120, and the camera 130, is moved to a position at which empty portion on the inspection board 150 is as small as possible, the captured image may preferably be acquired. Thereafter, the lighting intensity of the inspection apparatus 100 is established through adjusting a histogram of the captured image.

Figure 4A:
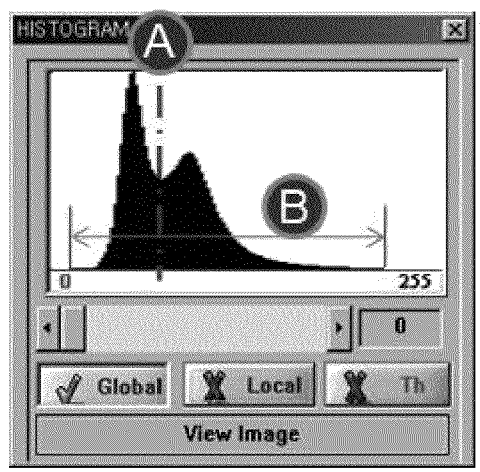
FIGS. 4A and 4B are captured images illustrating adjusting a histogram.
Figure 4B:
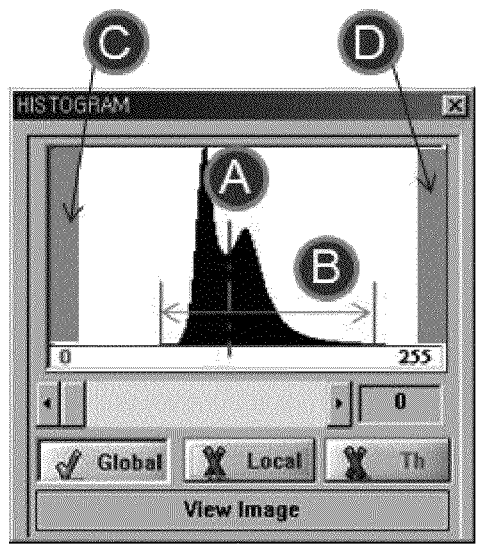

FIGS. 4A and 4B are captured images illustrating adjusting a histogram. FIG. 4A shows a histogram of a captured image, and FIG. 4B shows a histogram after adjustment. In the histogram in FIGS. 4A and 4B, the x-axis indicates image brightness, and the y-axis indicates the number of pixels corresponding to the image brightness.

Referring to FIGS. 4A and 4B, adjusting the histogram may be performed by adjusting an average 'A' of the histogram to be near a middle of a graph, adjusting a width 'B' of the histogram to avoid from a dark region 'C' and bright region 'D', adjusting the width 'B' of the histogram to be narrow, etc. The lighting intensity is established to have a range as narrow as possible through the histogram adjustment, and thus optimized range of the lighting intensity corresponding to the characteristic of the inspection board 150 may be established.

A measurable gray scale is in a range of 0 to 255 in a camera. In case that the histogram is near a middle of a graph, the measured lighting intensity becomes in the range of the measurable gray scale in a camera. Thus, in order to increase the number of pixels allowing the lighting intensity to be measurable, the histogram may be adjusted to be near a middle of a graph.

In establishing the lighting intensity, a preferable range of the lighting intensity may be established by using a visual marking method, in which red color is marked at a portion having a value greater than or equal to a first point corresponding to a selected bright value, and blue color is marked at a portion having a value smaller than or equal to a second point corresponding to a selected dark value.

After establishing the lighting intensity, a reference visibility of the inspection apparatus 100 is established corresponding to the characteristic of the inspection board 150 in step S220. The reference visibility corresponds to a measurement variable for judging whether the inspection is effective or not, and may be established in a range of 0 to 1 by the user.

Figure 5A:
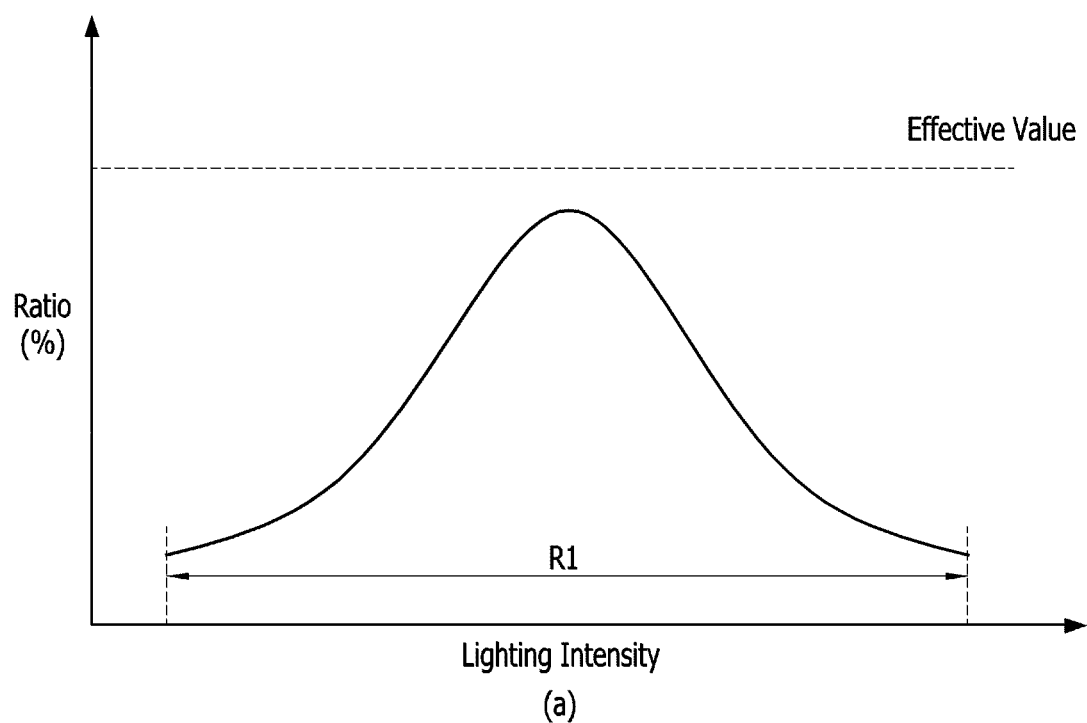
FIGS. 5A and 5B are graphs illustrating establishing a reference visibility.
Figure 5B:
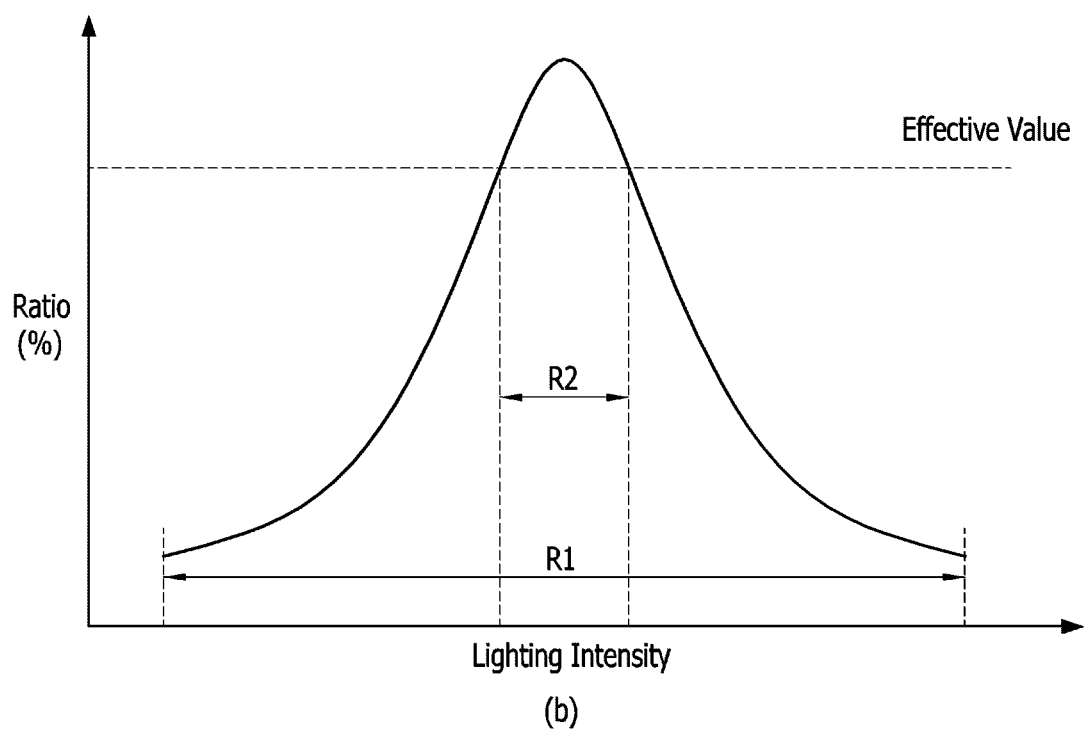

FIGS. 5A and 5B are graphs illustrating establishing a reference visibility. FIGS. 5A and 5B show a ratio of effective pixels having a visibility greater than the reference visibility according to change of the lighting intensity.

Referring to FIGS. 5A and 5B, in order to establish the reference visibility, visibility information is measured while changing an intensity of the lighting in a range of the lighting intensity established in step S210 of establishing the lighting intensity. As a result of measuring visibility information, as shown in FIG. 5A, a ratio of an effective pixel area to an area of an inspection region (or region of interest, ROI) may be not greater than an effective value that the user desires. The effective value corresponds to a value pre-established by the user, and may be established, for example, about 95%. In other words, in case that the reference visibility is too high established according to the characteristics such as color, reflectance, etc. of the inspection board 150, the ratio of the effective pixel area does not exceed the effective value. Thus, since it is difficult to perform an effective inspection, the reference visibility may preferably be re-established according to the characteristics of the inspection board 150. Hence, the reference visibility is established so that the ratio of the effective pixel area to the area of the inspection region, for example, a total area of the inspection region exceeds the previously established effective value in the measured visibility information. For example, while measuring the change of the ratio of the effective pixel area with changing the reference visibility, a visibility at which the ratio of the effective pixel area exceeds the effective value may be obtainable, as shown in FIG. 5B, and the obtained visibility is established as the reference visibility.

At least one of a region corresponding to the effective pixels and a region not corresponding to the effective pixels may be visually indicated in advance through the camera of the inspection apparatus by using the measured visibility information.

Thereafter, the lighting intensity established in step S210 of establishing the lighting intensity and the reference visibility established in step S220 of establishing the reference visibility are stored in step S230.

As described above, since the optimized lighting intensity and the optimized reference visibility are automatically re-established corresponding to inspection boards 150 having various characteristics, effective inspections may be performed for the various inspection boards 150 and inspection reliability may be enhanced.

While establishing the lighting intensity or the reference visibility, information of a specific region in which hole, silk, etc. is formed except for a pad region in which solder will be really formed in the inspection region may be acquired, and the information may be used in an actual inspection process, which is performed later, to thereby enhance inspection reliability.

Figure 6:
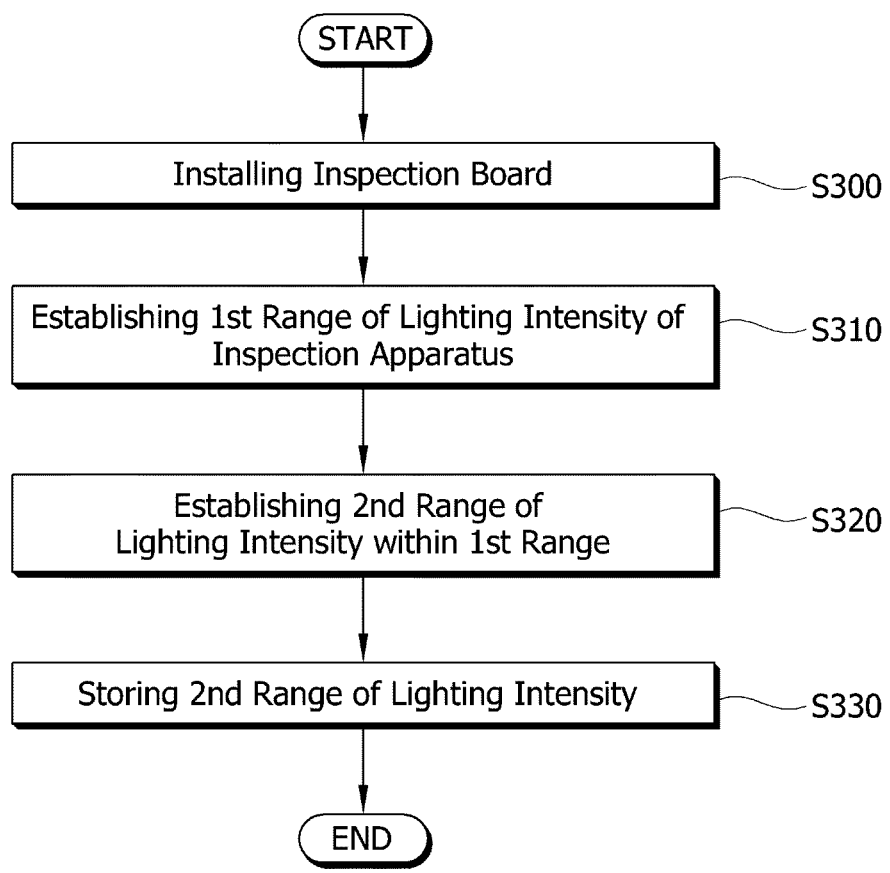
FIG. 6 is a flow chart showing a method of establishing a measurement variable of an inspection apparatus according to another exemplary embodiment of the present invention.

FIG. 6 is a flow chart showing a method of establishing a measurement variable of an inspection apparatus according to another exemplary embodiment of the present invention.

Referring to FIGS. 1 and 6, in order to establish the measurement variable of the inspection apparatus 100 corresponding to the characteristic of the inspection board 150, the inspection board 150 is installed on the stage 140 in the inspection apparatus 100 in step S300.

Then, a first range of the lighting intensity of the inspection apparatus 100 is automatically established corresponding to the characteristic of the inspection board 150 in step S310. Establishing the first range of the lighting intensity may be performed by adjusting the histogram of the captured image acquired from the camera 130 of the inspection apparatus 100. Adjusting the histogram may be performed by adjusting an average 'A' of the histogram to be near a middle of a graph, adjusting a width 'B' of the histogram to avoid from a dark region 'C' and bright region 'D', adjusting the width 'B' of the histogram to be narrow, etc. A range of the lighting intensity, corresponding to the width 'B' of the histogram, is a first range R1 of the lighting intensity. The first range R1 of the lighting intensity may be first established according to the characteristic of the inspection board 150 through the histogram adjustment. In establishing the first range R1 of the lighting intensity, the first range R1 of the lighting intensity may be established by using a visual marking method, in which red color is marked at a portion having a value greater than or equal to a first point corresponding to a selected bright value, and blue color is marked at a portion having a value smaller than or equal to a second point corresponding to a selected dark value.

Thereafter, a second range R2 of the lighting intensity of the inspection apparatus 100 is automatically established by using effective index information in the first range R1 of the lighting intensity in step S320. The effective index information may include, for example, visibility information.

In order to establish the second range R2 of the lighting intensity, visibility information is measured while changing an intensity of the lighting in the first range R1 of the lighting intensity established in step S310 of establishing the first range R1 of the lighting intensity. Then, as shown in FIG. 5B, as a result of measuring the visibility information, a range of the measured visibility information, in which a ratio of an effective pixel area to an area of an inspection region, for example, a total area of an inspection region exceeds a pre-established effective value, is established as the second range R2 of the lighting intensity.

At least one of a region corresponding to the effective pixels and a region not corresponding to the effective pixels may be visually indicated in advance through the camera of the inspection apparatus by using the measured visibility information.

Thereafter, the established second range R2 of the lighting intensity is stored in step S330.

As described above, the first range R1 is established by analyzing the histogram for the lighting intensity of the inspection apparatus 100, and then the second range R2 established in the first range R1 by using the visibility information, so that the lighting intensity may be minutely established according to the characteristic of the inspection board 150. Inspection may be performed in the established second range R2 of the lighting intensity, to thereby increase inspection precision. In establishing the lighting intensity, information of a specific region of a hole, a silk, etc. except for a pad region in which solder will be really formed in the inspection region may be acquired, and the information may be used in an actual inspection process, which is performed later, to thereby enhance inspection reliability.

Figure 7:
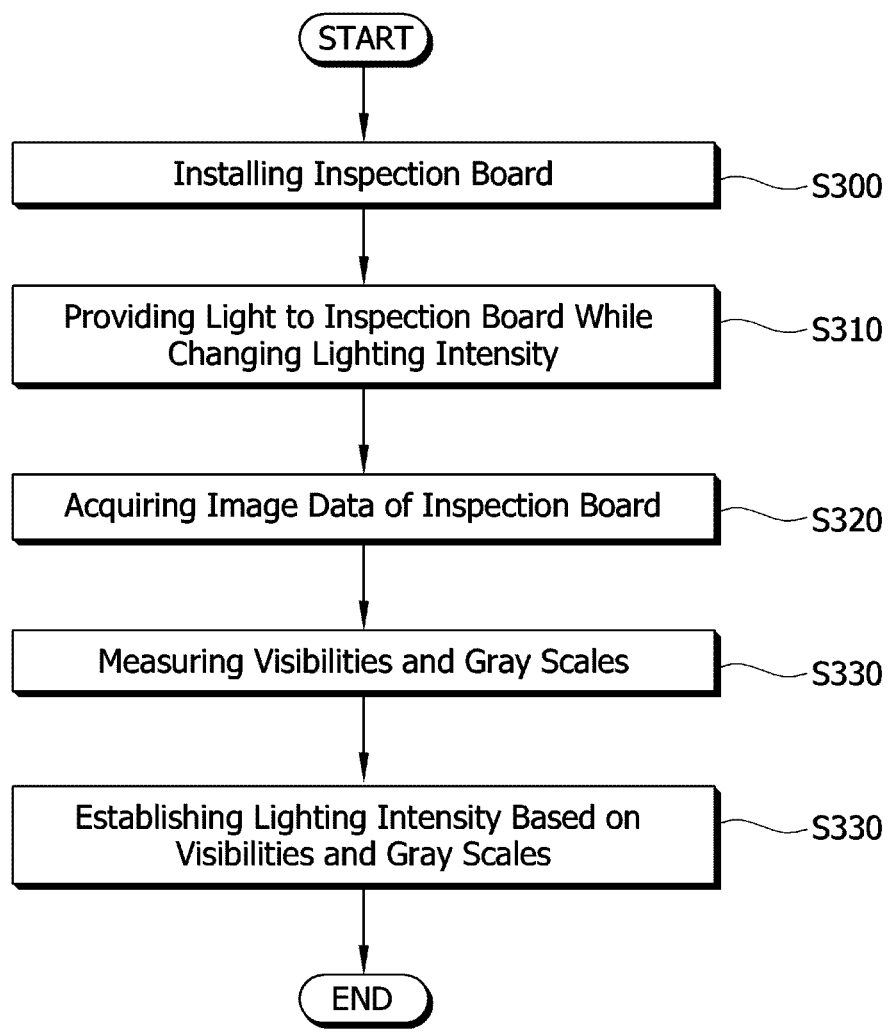
FIG. 7 is a flow chart showing a method of establishing a measurement variable of an inspection apparatus according to still another exemplary embodiment of the present invention.

FIG. 7 is a flow chart showing a method of establishing a measurement variable of an inspection apparatus according to still another exemplary embodiment of the present invention.

Referring to FIGS. 1 and 7, in order to establish a measurement variable of the inspection apparatus 100 according to the characteristic of the inspection board 150, the inspection board 150 is installed on the stage 140 in the inspection apparatus 100 in step S400.

Then, after light is provided to the inspection board 150 while changing the lighting intensity of the first lighting section 110 of the inspection apparatus 100 in step S410, the light reflected by the inspection board 150 is acquired through the camera 130 of the inspection apparatus 100 and the image data of the inspection board 150 according to the lighting intensity is acquired in step S420.

Thereafter, a visibility and a gray scale for each pixel are acquired from the acquired image data of the inspection board 150 in step S430. That is, the visibility and the gray scale for each pixel are measured for each of the image data captured for the lighting intensity.

Then, the lighting intensity of the first lighting section 110 is established based on the visibility and the gray scale in step S440. For example, the number of effective pixels in the image data of the inspection board 150 (the visibility and the gray scale are within a predetermined effective range at the effective pixels) is counted, and then the lighting intensity of the first lighting section 110 is established with an intensity of lighting allowing the number of effective pixels to be greater than or equal to a threshold. Alternatively, the lighting intensity of the first lighting section 110 is established with an intensity of lighting allowing a sum of the visibilities of effective pixels in the image data of the inspection board 150 (the visibility and the gray scale are within a predetermined effective range at the effective pixels) to be greater than or equal to a threshold. In other words, the effective pixels are produced based on the gray scale and the visibility for each image data acquired for each lighting intensity, and then an intensity of lighting corresponding to image data allowing the number of the effective pixels, a sum of the visibilities of the effective pixels, etc. to be greatest may be established as the lighting intensity of the first lighting section 110.

At least one of a region corresponding to the effective pixels and a region not corresponding to the effective pixels may be visually indicated in advance through the camera of the inspection apparatus by using the measured visibility information.

A measurable gray scale is in a range of 0 to 255 in a camera. Thus, in order to measure a three dimensional shape by using pattern light in a phase-shift moire measurement type, when a light intensity of a sinusoidal wave form is in a change range of 0 to 255 due to interference effect of light, a sinusoidal wave form is measurable without distortion such as below 0 or above 255 leaving a sinusoidal wave form in an inspection region. Thus, a threshold between 0 and 255, for example, 10 and 230 is set up, to establish a lighting intensity so that a sinusoidal wave form may not be distorted. That is, a gray scale may be used as a variable for establishing a lighting intensity.

A visibility is used to measure quality of a sinusoidal wave form for measured data, and judge whether measured data has great reliability or not. In order to acquire measured data having great reliability, a lighting intensity may be established to acquire a sinusoidal wave form in which a visibility is secured above a threshold. That is, a visibility may be used as a variable for establishing a lighting intensity.

When board characteristics such as color, reflectance, etc. are input by a user or by using a method of establishing a lighting intensity, a lighting intensity and a visibility are automatically established in previously established ranges to produce an optimized parameter. Thus, a setting time of a job file may be reduced, and precision may be enhanced. That is, an inspection condition of a job file is automatically re-established to correspond to a measurement target, thereby reducing measurement error.

As described above, the current hardware condition of the inspection apparatus 100 is checked by using the automated test program, and thus it may be judged whether the current working condition is proper or not in comparison with the initial hardware condition when the inspection apparatus is produced. In addition, measurement variables such as lighting intensity, reference visibility, etc. corresponding to the inspection boards 150 having various characteristics are automatically re-established, thereby reducing a setting time of an inspection condition stored in a job file to increase the user's convenience and reducing measurement error due to misestablishment to enhance inspection precision.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of establishing a lighting intensity of an inspection apparatus, comprising:

installing a printed circuit board in the inspection apparatus;

acquiring an image of the printed circuit board through a camera of the inspection apparatus to obtaining a histogram representing a distribution of brightness of the image, wherein an x-axis of the histogram represents a gray level and a y-axis of the histogram represents a number of pixels corresponding to the gray level;

adjusting the lighting intensity of the inspection apparatus by adjusting a width of the histogram as a whole to avoid a dark region and a bright region without changing an appearance of the histogram; and adjusting the lighting intensity of the inspection apparatus so that a mean value of the histogram is placed near a middle of the histogram.

2. The method of claim 1, further comprising adjusting the width of the histogram to be narrow.

3. The method of claim 1, further comprising adjusting the lighting intensity of the inspection apparatus by using an effective index information having a parameter corresponding to an average of the lighting intensity.

4. The method of claim 3, wherein the effective index information includes visibility information.

5. The method of claim 4, wherein adjusting the lighting intensity of the inspection apparatus includes:

measuring visibility information while changing the lighting intensity of the inspection apparatus; and establishing the lighting intensity of the inspection apparatus with an intensity of lighting allowing a ratio of an effective pixel area to an area of an inspection region to exceed a pre-established effective value in the measured visibility information.

6. The method of claim 5, after measuring the visibility information with changing the lighting intensity of the inspection apparatus, further comprising visually indicating at least one of a region corresponding to effective pixels and a region not corresponding to the effective pixels in advance through the camera of the inspection apparatus by using the measured visibility information.

7. The method of claim 1, wherein the lighting of the inspection apparatus corresponds to grating pattern lighting.

8. The method of claim 1, further comprising:

before adjusting the width of the histogram, marking a first color at the dark region having a value smaller than or equal to a selected dark value, and a second color is marked at the bright region having a value greater than or equal to a selected bright value.

* * * * *